(12) United States Patent  (10) Patent No.: US 7,789,583 B2
Kuo  (45) Date of Patent: Sep. 7, 2010

(54) MANUAL AND ELECTRICAL PUMP TOOTHBRUSHES FOR DISPENSING LIQUID AND PASTE DENTIFRICES

(76) Inventor: Youti Kuo, 88 Foxbourne Rd., Penfield, NY (US) 14526

( * ) Notice: Subject to any disclaimer, the term of this patent is extended or adjusted under 35 U.S.C. 154(b) by 804 days.

(21) Appl. No.: 11/206,716

(22) Filed: Aug. 19, 2005

(65) Prior Publication Data

US 2007/0041779 A1    Feb. 22, 2007

(51) Int. Cl.
*A46B 11/02*  (2006.01)
(52) U.S. Cl. ............ 401/188 R; 401/270; 401/278
(58) Field of Classification Search ............ 401/188 R, 401/270, 278, 279, 282, 291
See application file for complete search history.

(56) References Cited

U.S. PATENT DOCUMENTS

| 5,393,153 | A | * | 2/1995 | Bouthillier et al. | ......... 401/146 |
| 5,746,532 | A | * | 5/1998 | Megill et al. | ........... 401/175 |
| 5,769,585 | A | * | 6/1998 | Podolsky | ............. 401/146 |
| 5,909,977 | A | | 6/1999 | Kuo | |
| 6,241,412 | B1 | | 6/2001 | Spies et al. | |
| 6,808,331 | B2 | | 10/2004 | Hall et al. | |

* cited by examiner

*Primary Examiner*—David J Walczak

(57) ABSTRACT

Pump toothbrush comprising a refillable cartridge containing dentifrice material, a pump head having an elastic compressible button, and a brush head having a spout opening attached with a slit valve. The slit valve prevents backflow and drying of the dentifrice material at the spout opening. The slit valve opens and closes automatically with the pumping action. The dispensing mechanism and cartridge structure are applicable to manual and electrical pump toothbrushes.

1 Claim, 8 Drawing Sheets

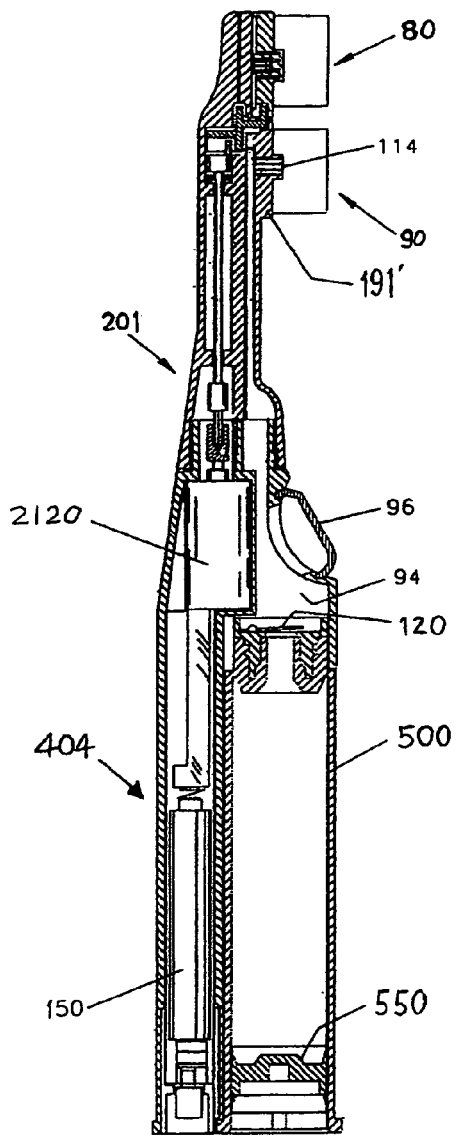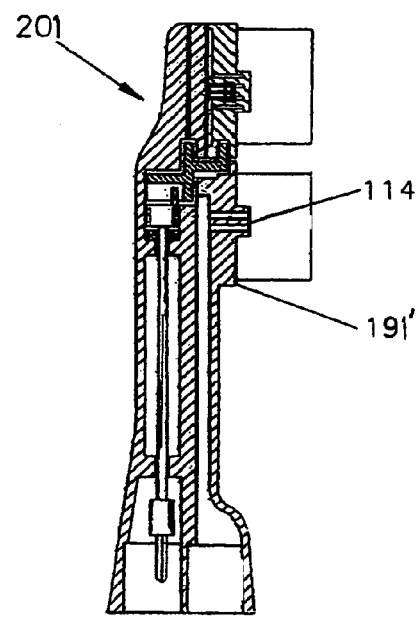
Fig. 5a
Fig. 5b

MANUAL AND ELECTRICAL PUMP TOOTHBRUSHES FOR DISPENSING LIQUID AND PASTE DENTIFRICES

BACKGROUND OF THE INVENTION

It is known that liquid dentifrice outperforms traditional viscous paste dentifrice in plaque removal because of liquid format that can easily penetrate into narrow spaces between teeth. In comparisons, paste dentifrices are too thick to penetrate these tiny spaces even with fine bristle. Therefore, the most effective method of teeth cleaning and plaque removal is a combination of applying and containing liquid dentifrice with bristles on tooth surfaces and in spaces between teeth while brushing. Furthermore, for better flow control, it is preferable to have incremental dispensing of liquid dentifrice without interrupting the continuous brushing motion.

For accomplishing brushing with liquid dentifrice, there are many features to be provided in a toothbrush for achieving the most effective and efficient brushing. A pump toothbrush must enable repeated pumping actions conveniently with one hand for dispensing incrementally without interrupting the brushing motion. The toothbrush should ensure full efficiency in dispensing expected amount of dentifrice at each pumping action that does not induce backflow and voids in the brush head. Furthermore, since paste dentifrices are being used by consumers, such a manual or electrical pump toothbrush is desirable to dispense any liquid and paste dentifrices while satisfying the above incremental dispensing and no backflow requirements.

(1) Field of the Invention

The present invention relates to a pump toothbrush using an elastic compressible button for repeated pumping during brushing and a piston-cartridge for the packing of liquid or paste dentifrice for reliable pumping. In particular it relates to means of delivering liquid dentifrice directly on teeth surfaces for maximum cleaning efficiency as well as a means of self-closing spout opening for preventing backflow and drying of dentifrice material in the brush head.

(2) Description of the Prior Art

There have been many patents in the prior art of dentifrice dispensing toothbrush. U.S. Pat. No. 5,909,977 by Kuo provides a dentifrice dispensing toothbrush for dispensing paste dentifrice with a paste or piston cartridge. A piston cartridge uses a piston for packing the dentifrice material for reliable pumping. However, the toothbrush does not provide positive means of preventing backflow and voids in the brush head in case of using liquid dentifrice. Due to low viscosity a liquid dentifrice material in the brush head can be freely sucked back into the pumping chamber as the elastic compressible button is released from a depressed position to its free-state position. The back flow causes voids in the flow channel of the brush head that leads to poor pumping efficiency as less amount of dentifrice being dispensed at each pumping action.

For dispensing liquid dentifrice, U.S. Pat. No. 6,241,412 by Spies et al. uses a pump assembly having an inlet port attached with an inlet needle for sucking liquid dentifrice stored in a cartridge. The concept is only for dispensing liquid dentifrice, pre-excluding the use of paste dentifrice as the inlet needle cannot suck viscous dentifrice material stored in the cartridge.

For dispensing dentifrice, U.S. Pat. No. 6,808,331 by Hall et al. describes a pump element located in the brush head portion of the toothbrush using the action of the moving brush head to move fluid from the on-board fluid reservoir to the bristles on the brush head. As a disadvantage, the fluid-dispensing system is not independent of the movement of the brush head. As a result, the dentifrice material is continuously dispensed while the brush head is being driven. In the powered toothbrush product with the trade name Intelliclean System of Sonicare and Crest manufactured by Philips and Procter & Gamble, specially formulated toothpaste is dispensed to the vibrating brush head for liquefying the toothpaste with high speed bristle motion to reach to hard-to-reach areas between teeth. The system requires special formulation of dentifrice material for transforming the dentifrice material into liquid form by spinning motion and it has a disadvantage that its dentifrice cartridge is not refillable by a user. It is preferable that liquid dentifrice of desirable viscosity can be directly dispensed for brushing without employing a complicated spinning mechanism and that a refillable cartridge be used for refilling by user for cost savings.

Furthermore, a dentifrice dispensing toothbrush is required to prevent drying of dentifrice material. For sealing the spout opening in the brush head, the U.S. Pat. No. 6,599,048 by Kuo uses a plug having a sealing rod shielded by an annular wall for engaging the spout wall of the opening in the brush head. The use of a plug is an extra step for sealing the spout opening, therefore, inconvenient for an user. In U.S. Pat. No. 5,746,532 by Megill, et al. a brush head is equipped with three slit valves. However, the closing of the valve elements requires an extra manual step of turning an actuator knob for creating a vacuum to withdraw toothpaste inward in the valve region. Since the valve closing is not automatic, neglecting the manual closing step may result in drying of the toothpaste. Therefore, it is desirable to have a self-closing spout that can automatically seal the dispensing opening after a pumping action.

(3) Objects of the Invention

It is an object of the present invention to provide a pump toothbrush with a pump head having an elastic compressible button for the convenience of repeated pumping during brushing with one hand and using a common pump head and a common cartridge for dispensing any liquid and paste dentifrices. It is also an objective to provide a self-closing spout opening for preventing backflow and drying of dentifrice material in the brush head. It is a further objective to meet these requirements for both manual and electrical pump toothbrushes.

SUMMARY OF THE INVENTION

In accordance with the present invention, a pump toothbrush is provided having common pump head and cartridge structures for dispensing any kinds of liquid and paste dentifrice materials for repeated pumping with one hand during brushing and for preventing backflow. The pump head using a resilient elastic compressible button for pumping is provided with an outlet connector for mounting replaceable brush head and an inlet connector for mounting a piston-cartridge. The elastic button is located at the thumb position for the convenience of repeated pumping anytime in continuous brushing motion. Additionally, a self-closing slit valve is attached to the spout opening for preventing backflow and drying of dentifrice material at the spout opening. The slit valve is forced to open by exiting dentifrice and to close by the vacuum force and the resiliency of rubber material when the elastic button is released from the pumping. In addition, the above dispensing mechanism and cartridge structure are applicable to manual and electrical pump toothbrushes.

BRIEF DESCRIPTION OF THE DRAWINGS

FIG. 1b is a section view of an assembled pump toothbrush of FIG. 1a.

FIG. 5a is a section view of an electrical pump toothbrush with a dual-channel brush head having a rotary and a stationary bristle unit.

FIG. 5b is a section view of a dual-channel brush head having a multi-orifice spout opening.

DETAILED DESCRIPTIONS OF THE PREFERRED EMBODIMENT

Figure 1A:
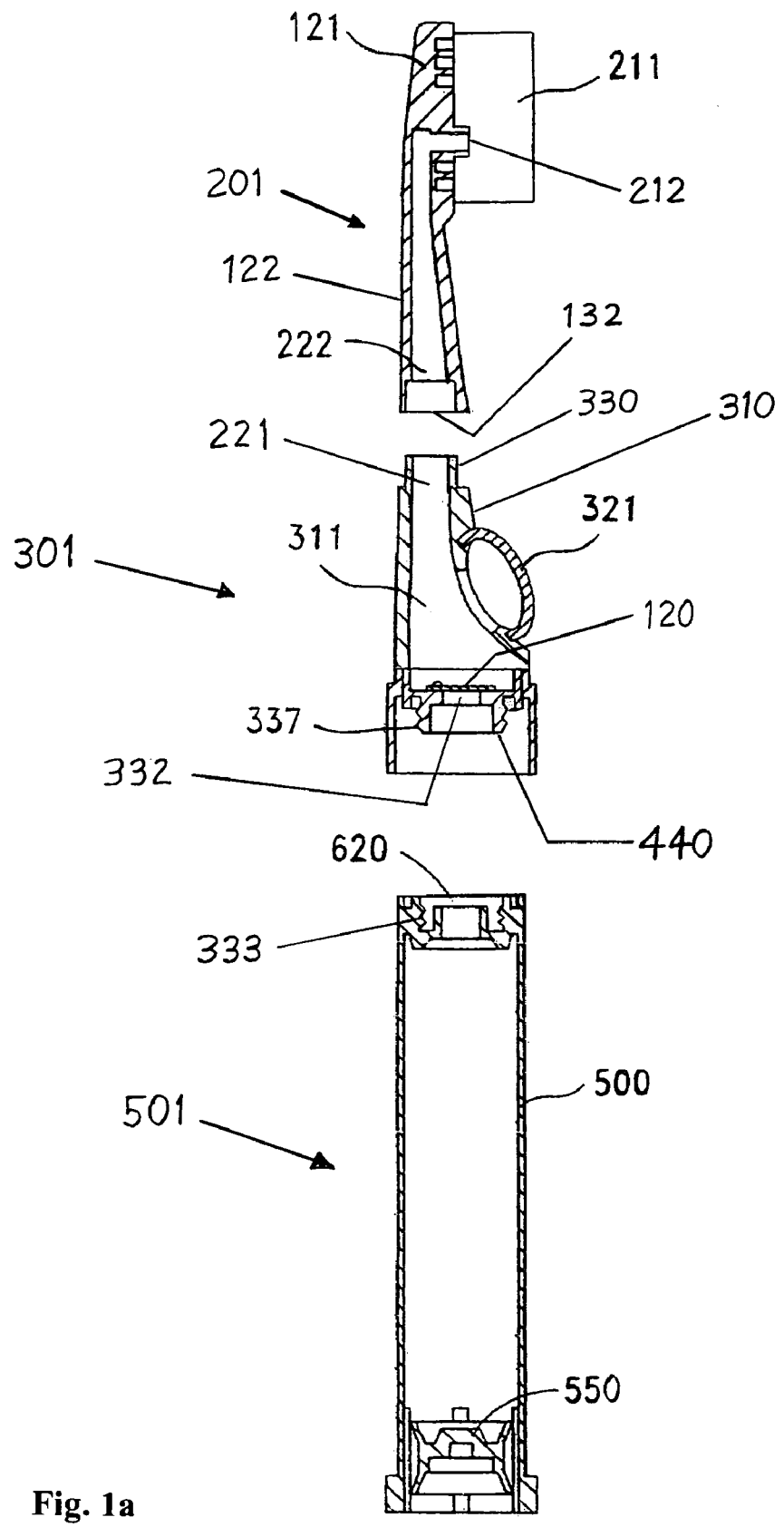
FIG. 1a is a perspective view of an unassembled pump toothbrush of the present invention with a brush head, a pump head and a piston-cartridge.

Throughout the following detailed description, same reference numerals refer to the same elements in all figures.

Figure 1B:
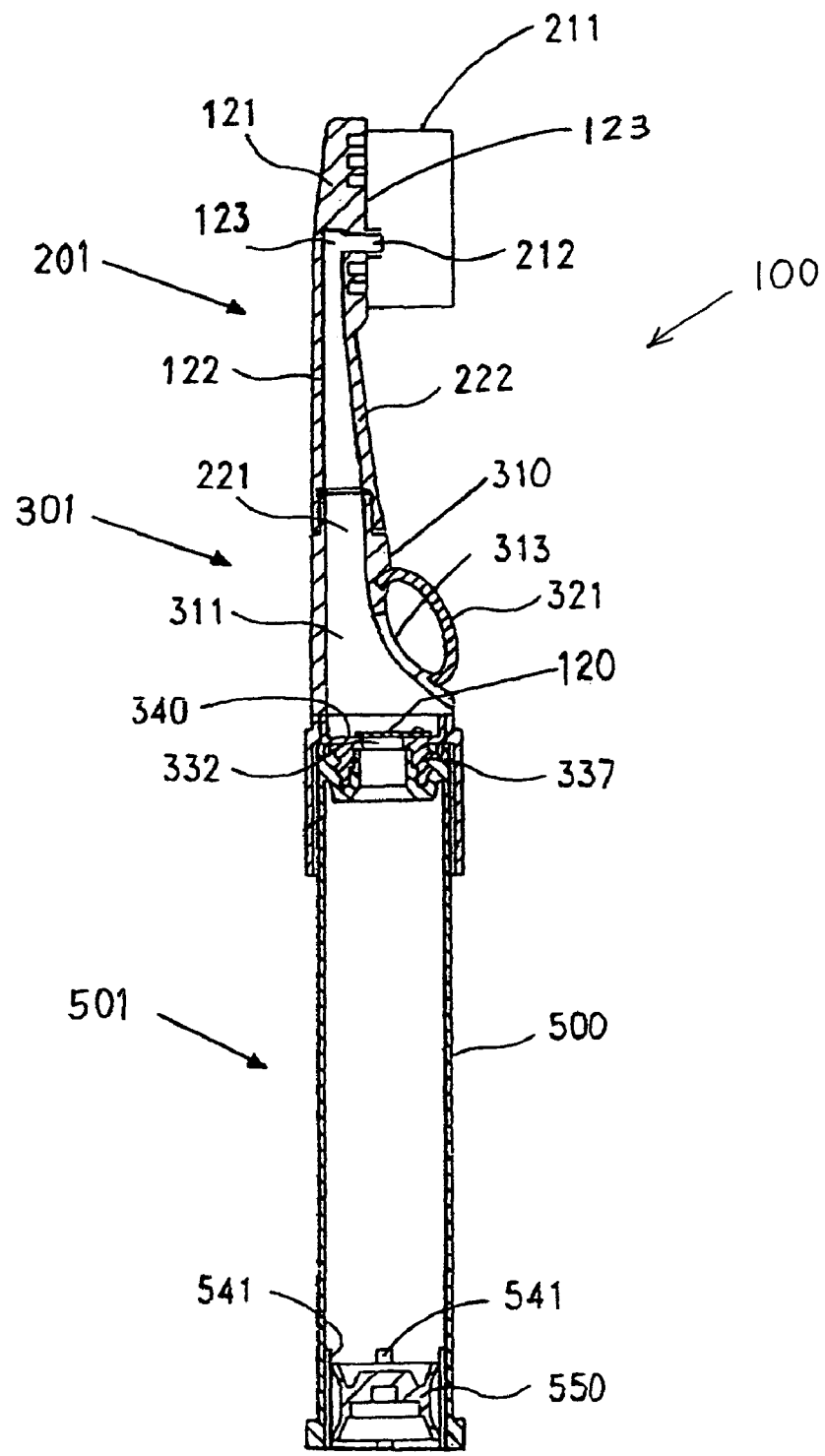

A pump toothbrush of this invention includes a replaceable brush head, a pump head and a dentifrice cartridge. FIG. 1a shows brush head 121 and cartridge 501 being detached from pump head 301 which has inlet connector 440 and outlet connector 330. Both the inlet connector and the outlet connector are supported by sidewall 310. FIG. 1b shows an assembled pump toothbrush 100 having cartridge 500 attached to inlet connector 440 and brush head 121 attached to outlet connector 330. As shown in FIG. 1b, brush head 121 having platform 123 with bristles 211 and outlet opening 212, neck 122 having flow channel 222. Neck 122 is mounted on outlet connector 330 with flow channel 222 in communication with flow channel 221 of outlet connector 330, whose outer tubular wall surface is mated with the inner surface of flow channel 222 at base 132. Pump head 301 has pump chamber 311 which is in communication with inlet connector 440 and outlet connector 330, and dome-shaped resilient elastic compressible button 321 which is attached to opening 313 on rigid sidewall 310 between the inlet and the outlet connectors. Elastic button 321 is used to supply a pumping force inside pumping chamber 311 which causes dentifrice material (not shown) to flow from cartridge 500 to brush head 121. Exterior threads on recess wall 337, which is attached to the exterior surface of inlet connector 440 with inlet opening 332 therethrough, and interior threads 333 of cartridge 500 are engaged for fastening cartridge 500 to pump head 301. The elastic button is positioned for pressing by the thumb with the brush toothbrush being held in the hand. The combination of attaching the elastic compressible button to the rigid sidewall and the position of the elastic button in the pump toothbrush enables repeated pumping with comport during brushing.

When a pumping force is applied by depressing elastic button 321, inlet check valve 120, which is attached to inner surface 340 of inlet connector 440, closes the opening 332 and it is at the open position when the pumping force is released. For a paste dentifrice material, the viscous resistance in flow channel 222 of brush head 201 hinders any backflow from the brush head through the outlet connector to the bump chamber. Consequently, the vacuum force inside the pump chamber created by the spring back motion of the elastic button induces the forward movement of the dentifrice material from the cartridge to the pump chamber that keeps the inlet check valve at open position. Referring to FIG. 1a and FIG. 1b, a piston-cartridge 501 consists of cylindrical tube 500 having interior threads 333 on outer annular wall extension at top opening end 620, a number of shallow vent grooves 541 on the inner surface of its bottom opening end. Piston 550 has upper annular rim and lower annular rim. Piston 550 is inserted into cylindrical tube 500 through bottom opening of cartridge 501 to provide slidable sealing of the dentifrice material. The piston-cartridge can be refilled with dentifrice material when empty by mounting its top opening end on a toothpaste tube by which dentifrice material can be squeezed into and to fill up the cartridge.

When compressible elastic button 321 is released from a depressed position after dispensing the dentifrice material, elastic button 321 returns to its original shape because of the resiliency and memory of the material from which it is made. At the same time, the dentifrice material in cavity of the dome-shaped elastic button, pump chamber and in cartridge reservoir moves with elastic button 321 while piston 550 advances to a new forward position that keeps the dentifrice material in a packed condition. Additional quantities of dentifrice material are dispensed through repeated pumping actions during brushing. In each pumping action, piston 550 is advanced inside of piston-cartridge 500. For a liquid or low-viscosity material, the viscous resistance in the flow channel of the brush head is at a low level that the vacuum force can induce backflow from the brush head to the pump chamber as well as the forward-flow from the cartridge to the pump chamber. Any backflow from the brush head creates a void near the spout opening, therefore, results in low pumping efficiency as less or no dentifrice material is dispensed to the brush head at the next pumping action.

Figure 2:
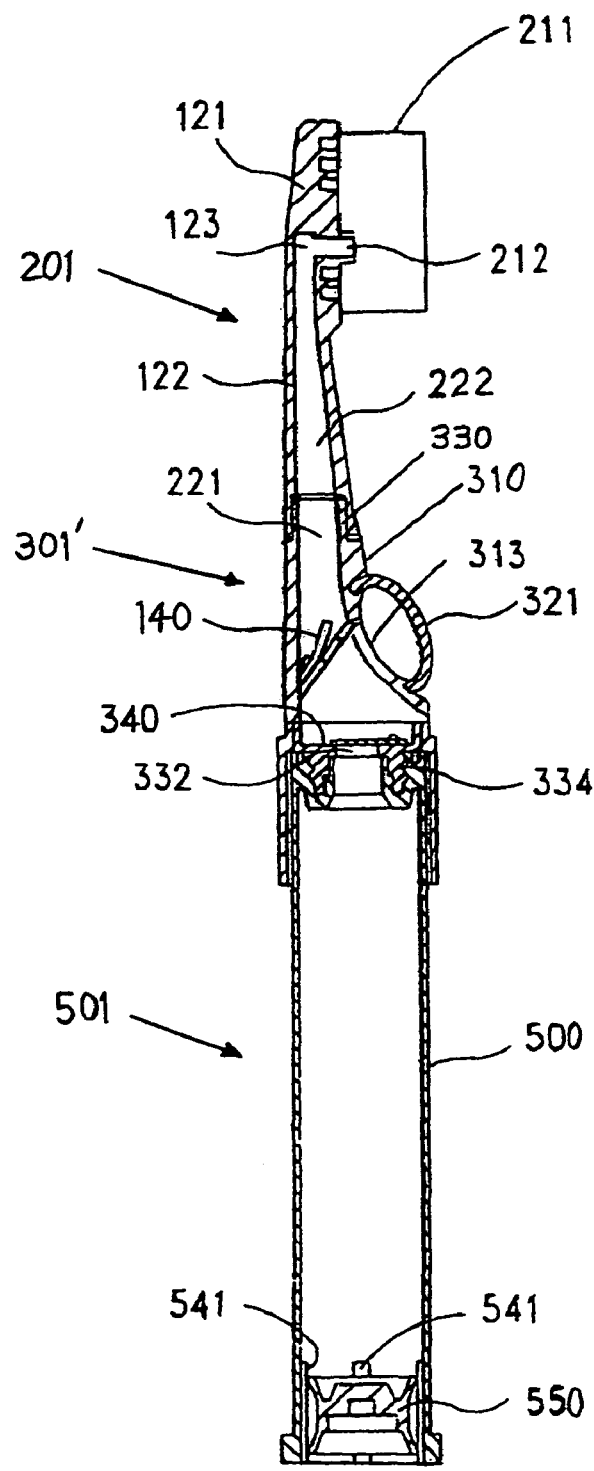
FIG. 2 is a section view of a pump toothbrush having an outlet check valve.

For preventing the backflow, one embodiment of the present invention is placing a one-way check valve at the entrance of the outlet connector. As shown in FIG. 2, pump head 301' has outlet check valve 140 positioned at the entrance of outlet connector 330. Here the entrance of the outlet connector is defined as any location in the flow path between sidewall opening 313 at the junction with the elastic compressible button and outlet opening at top end of outlet connector 330. Outlet check valve 140 is forced to an open position when the elastic button is being depressed for dispensing the dentifrice material, and simultaneously inlet check valve 120 is being forced to the closed position. On the other hand, outlet check valve 140 is forced to the closed position by the vacuum force generated inside the pump chamber when the elastic button is being released from the depressed position while at the same time the inlet check valve 120 being forced to open as described previously.

Figure 3C:
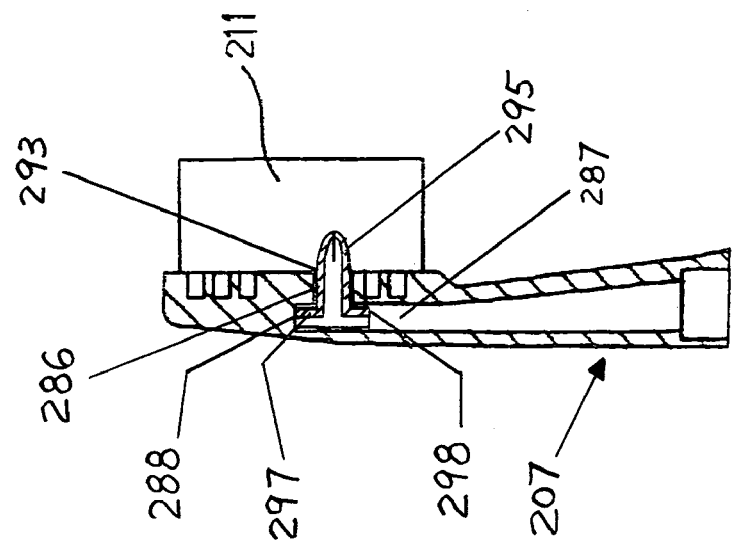
FIG. 3c is a section view of a brush head with a slit-valve inserted in the spout opening.
Figure 3B:
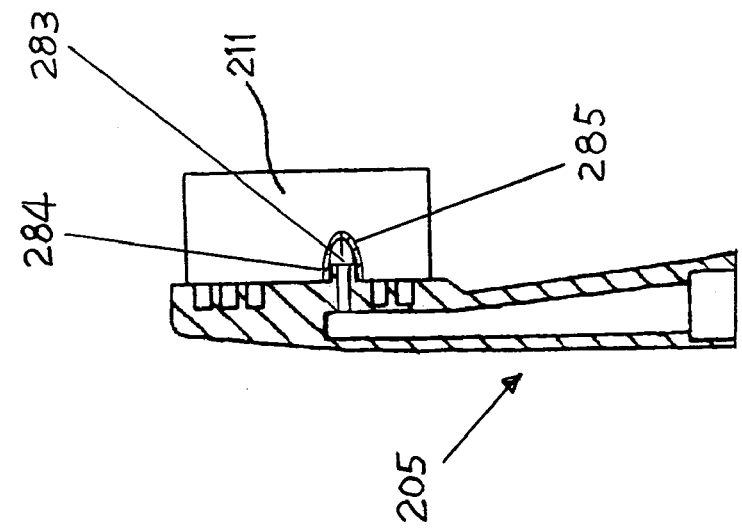
FIG. 3b is a section view of a brush head with a slit-valve attached to the spout-opening wall.
Figure 3A:
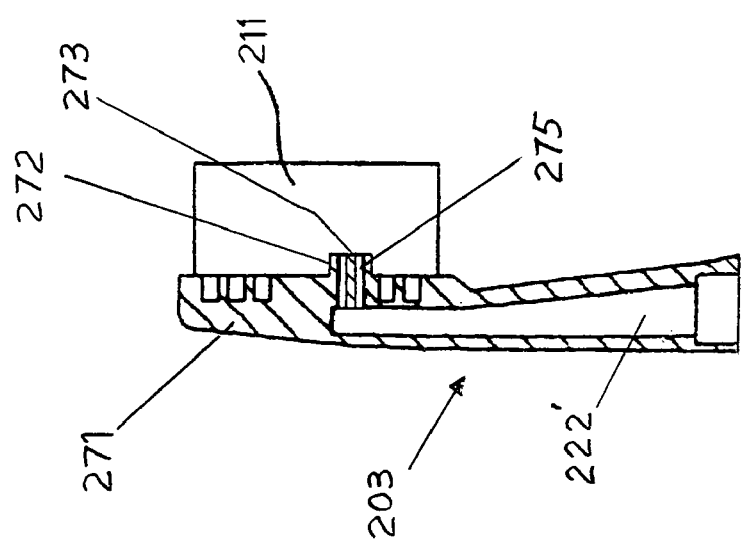
FIG. 3a is a section view of a brush head having multi-orifice in the spout opening.

Another embodiment of the present invention is the use of a multi-orifice spout opening in a brush head. FIG. 3a shows a replaceable brush head 203 having a multi-orifice spout opening 273. The multi-orifice brush head 203 is to replace the brush head 201 used in pump toothbrush 100 as shown in FIG. 1b, in which no outlet check valve is used. For distinguishing with a brush head having two or more spout openings, the multi-orifice spout opening 203 has a plural numbers of small orifices 275 extended from flow channel 222' without bristles between orifices 275 or these orifices are inside spout wall 272 extending from bristle platform 271. These small orifices are for creating liquid jets when liquid dentifrice is forced out from the spout opening by squeezing on the much larger elastic compressible button. The jet streams can deliver liquid dentifrice away from the spout opening and toward teeth surfaces if aimed during brushing. The multi-orifice spout opening also has the effect of hindering the backflow from the brush head to the pump chamber due to high flow resistance imposed by the small diameters of the orifices. With the multi-orifice in place, an outlet check valve is not necessary for preventing backflow.

A further embodiment of the present invention is the use of a cross-slit valve at the spout opening. FIG. 3b shows brush head 205 having cross-slit valve 285 attached on the wall of spout opening 283. Slit-valve brush head 205 is to replace the brush head 201 used in pump toothbrush 100 as shown in FIG. 1b, in which no outlet check valve is used. Cross-slit valve 285 has a tubular wall base 284 and the slit valve is preferably made of thermoplastic elastomer material for resiliency and injection molding. In a preferred embodiment a cross-slit valve has four flappers 285 forming a normally closed dome-shaped surface. Each flapper is a curved triangular valve segment extending from tubular wall 284 with tip of each valve segment intercepting at the center of the slit valve opening when the slit valve is closed. Each valve segment can be bent like a cantilever beam under the pressure of a dispensing flow. When a slit-valve brush head is used in a pump toothbrush of the present invention, the slit-valve is forced to open by exiting dentifrice material under the pumping pressure when the elastic compressible button is depressed. The slit valve closes after the elastic button is released. The slit length, wall thickness and the elastic modulus of the valve material are designed to ensure closing of the slit valve by the resiliency and the vacuum force when the pumping force is released. The height of a slit valve is below the bristle top surfaces such that the slit valve normally does not touch teeth during brushing but it enables delivery of dentifrice directly to teeth surfaces without spreading the dentifrice around at the base of the spout opening wall. With the use of a slit-valve brush head, it is not necessary to use an outlet check valve for preventing backflow. In manufacturing, a slit valve may be attached to the spout wall by adhesive bonding or by employing a heat gun assuming that the selected thermoplastic elastomer material is heat shrinkable.

Figure 5C:
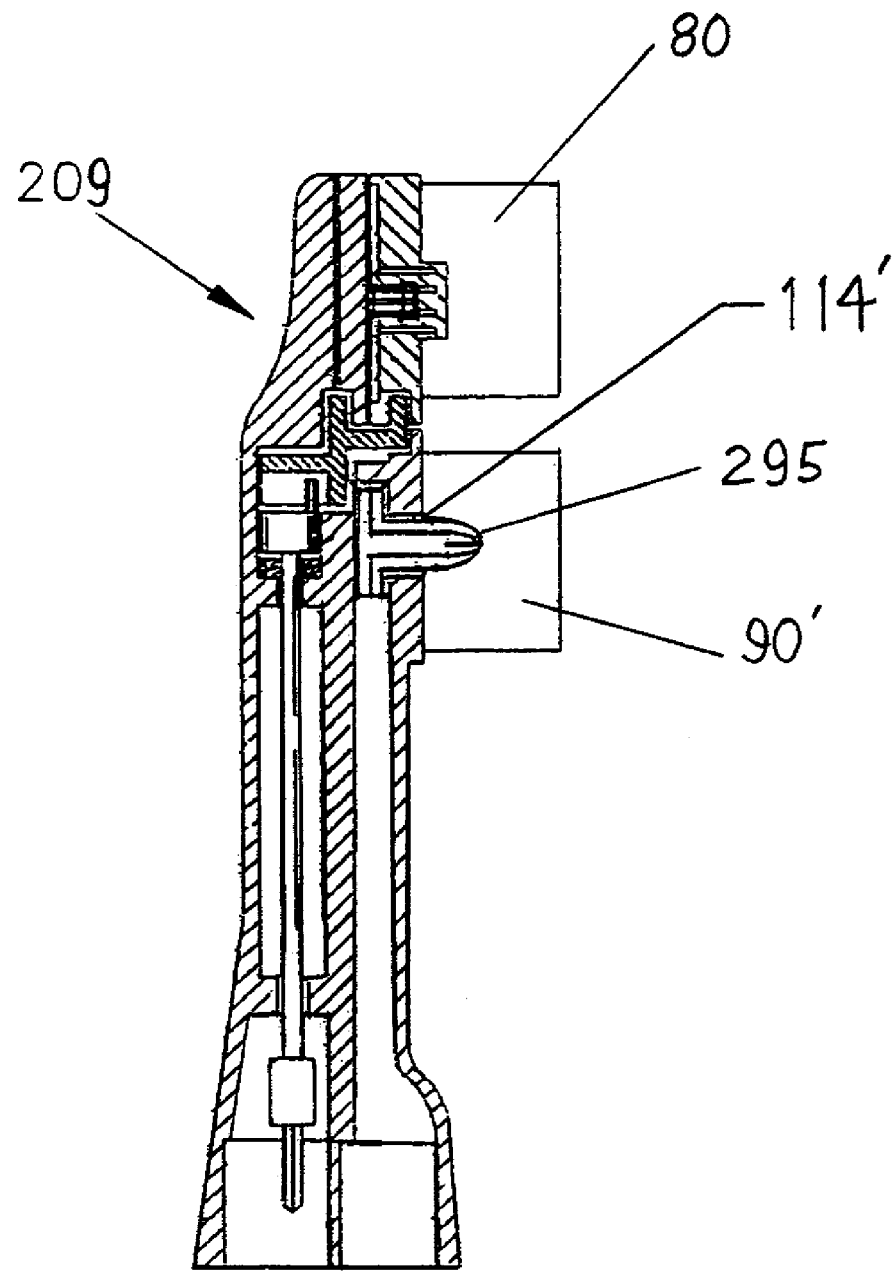
FIG. 5c is a section view of a dual-channel brush head having a slit-valve spout opening.

Alternatively, a cross-slit valve may be made as a snap-fit insert for attaching to a spout opening without using the adhesive bonding or the heat gun. FIG. 3c shows brush head 207 having snap-fit slit-valve insert 295 attached to spout opening 293. As shown in FIG. 3c, snap-fit slit valve insert 295 has first flange 297 and second flange 298, extending perpendicular to tubular wall 286 for fitting into the flow channel 287 in brush head 207. For firmly fitting into extended portion 288 of flow channel 287, first flange 297 has size and shape with dimensions and clearances that can be slipped into extended portion 288, which is indicated in FIG. 5c, by tilting slit-valve insert 295 to lead into the spout opening 293. For facilitating the insertion, spout opening 293 is of oval shape having a straight and parallel section in the middle for accommodating the thickness of first flanges 297 and second flange 298 for the insertion. After first flange 297 is pressed in, second flange 298 can be squeezed into spout opening 293 due to the compressibility of resilient tubular wall 286 The thickness of second flange is less than the corresponding width of the lead-in portion of flow channel 287 for not blocking the pumping flow. With first and second flanges snapped on in place and the tubular wall snugly fitted into the spout opening, the slit-valve is securely attached to the brush head. For reducing the opening pressure, a slit-valve is preferably made of silicone elastomer with inner contact surfaces coated with an adhesion-reducing compound if necessary.

The above described pumping mechanism and the use of piston-cartridge are applicable to an electrical pump toothbrush. Structures of electrical toothbrush that can dispense dentifrice materials are disclosed in U.S. Pat. Nos. 6,434,773, 6,735,803 and 6,902,337 by Kuo. However, these prior art patents do not specifically address the pumping requirements of liquid dentifrice materials. An electrical pump toothbrush of the present invention for dispensing liquid and paste dentifrice materials has either a pump handle having a dual-channel outlet connector with an outlet check valve or a dual-channel brush head having a multi-orifice or a slit-valve spout opening.

Figure 4:
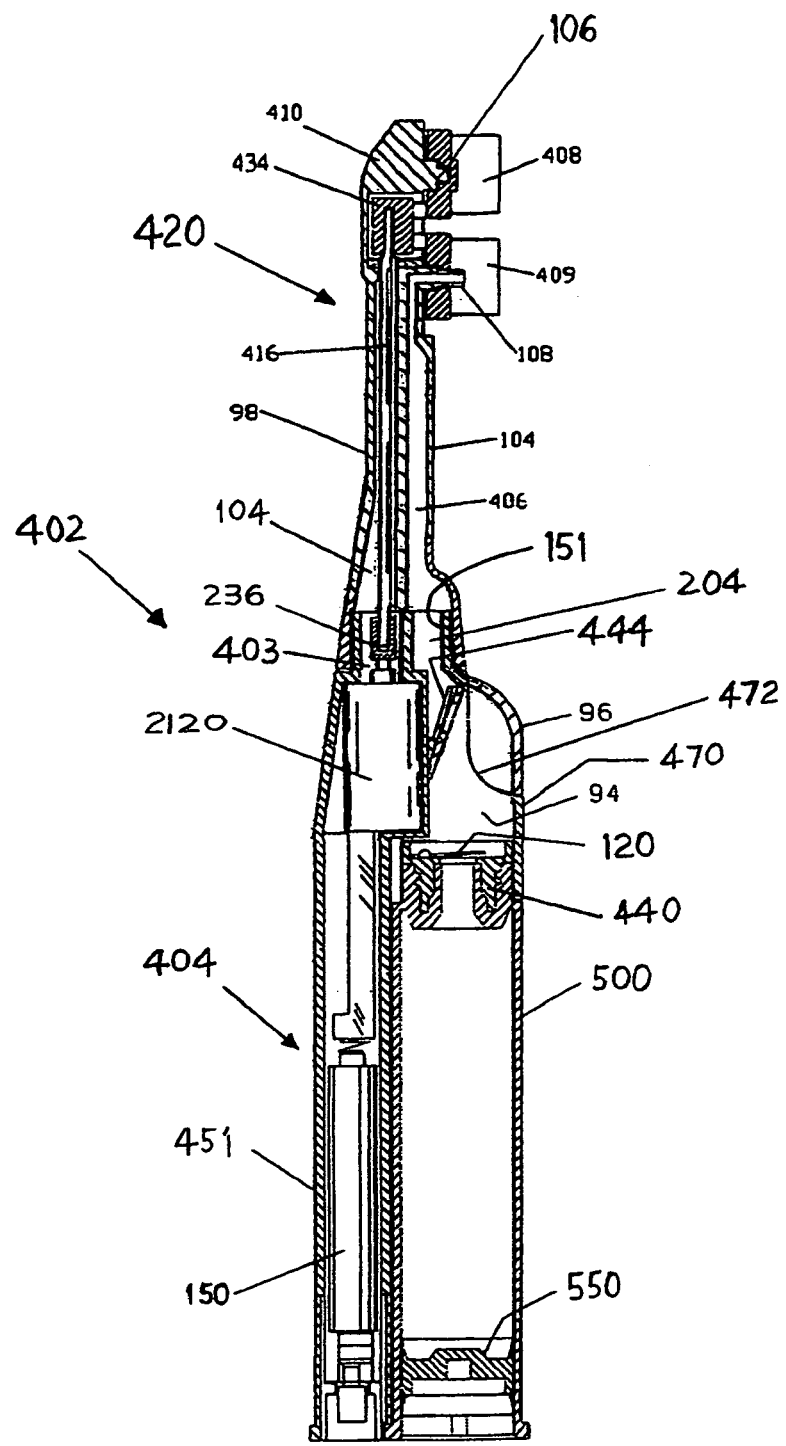
FIG. 4 is a section view of an electrical pump toothbrush with a dual-channel brush head having two rotary bristle units and a pump handle having an outlet check valve.

In accordance with these embodiments, an electrical pump toothbrush 402, as shown in FIG. 4, has dual-channel brush head 410, pump handle 404 and cartridge 500. Pump handle 404 has housing 451 with sidewall 470 and opening 472 which is attached with elastic compressible button 96. The dual-channel brush head 420 consists of rotary bristle units 408 and 409, platform 410 with post 106 and spout-opening post 108, dual-channel neck 98 having first drive shaft 416 in first drive channel 104 and first flow channel 406, which extends to spout opening 108. The top end of dual-channel neck 98 is connected to platform 410 and the bottom end is for detachable mounting on outlet dual-channel connector 151. Outlet dual-channel connector 151, which has tubular wall extending from side wall 470, has second drive channel 403 containing second drive shaft 236 and outlet flow channel 204 for connecting to first flow channel 406 of brush head 420 when mounted. Similar to the manual pump toothbrush described previously, elastic button 96 is positioned for pressing by the thumb when pump handle 404 is held in the hand. The combination of attaching elastic compressible button 96 to opening 472 on rigid sidewall 470 and the position of elastic button 96 in pump toothbrush 402 enables repeated pumping with comport in continuous brushing motion. The oscillation motion of the bristle units has been adequately described in prior art. Briefly, tab 434 extends radially outward from the central longitudinal axis of drive shaft 416 and engages with notches of bristle unit 408 and 409 such that the oscillation of the drive shaft 416 and tab 434 driven by motor 2120 with battery 150 causes bristle unit 408 and 409 to freely oscillate on post 106 and spout-opening post 108.

As shown in FIG. 4, an electrical pump toothbrush of the present invention adds an outlet one-way check valve 444 at the entrance of the outlet dual-channel connector 151 for positively blocking backflow. The structure and functions of outlet check valve 444 for electrical pump toothbrush 402 is the same as that for a manual pump toothbrush as described in preceding sections. Outlet check valve 444 is forced to an open position when the elastic button is being depressed for dispensing the dentifrice material and the outlet check valve is forced to the closed position when the elastic button is released. Similarly, inlet check valve 120 is movably attached to inlet connector 440 and it closes and opens in response to the pumping action as described previously.

In another configuration as shown in FIG. 5a, dual-channel brush head 201 has rotary bristle unit 80 and stationary bristle unit 90 and the latter has spout-opening post 114 through bristle platform 191'. The drive and flow communication between dual-channel brush head 201 and pump handle 404 are similar to that of dual-channel brush head 420 which has two rotary brush heads as described in FIG. 4. A detailed description of the drive mechanism for one rotary and one stationary bristle unit is given in U.S. Pat. No 6,902,337 by Kuo. In the present invention, without using an outlet check valve, multi-orifice or a slit valve is optionally used in the spout opening for blocking the backflow of dentifrice material in a dual-channel brush head. FIG. 5b shows an enlarged view of the dual-channel brush head 201 of FIG. 5a having multi-orifice spout-opening post 114 and FIG. 5c shows a dual-channel brush head 202 having slit-valve 295 at spout opening 114'. The functions and configurations of the multi-orifice and the slit-valve spout openings are the same as that described previously for the manual toothbrush. Note that these multi-orifice and slit-valve configurations as shown in FIG. 5b and FIG. 5c are applicable to a dual-channel brush head having two rotary bristle units.

For preventing drying of dentifrice at the spout opening of a pump toothbrush in general, a toothbrush container is provided in the present invention. The toothbrush container of the present invention is especially for preventing drying of dentifrice at an un-sealed spout opening, such as the aforementioned multi-orifice spout opening.

Figures 6A, 6B, 6C:
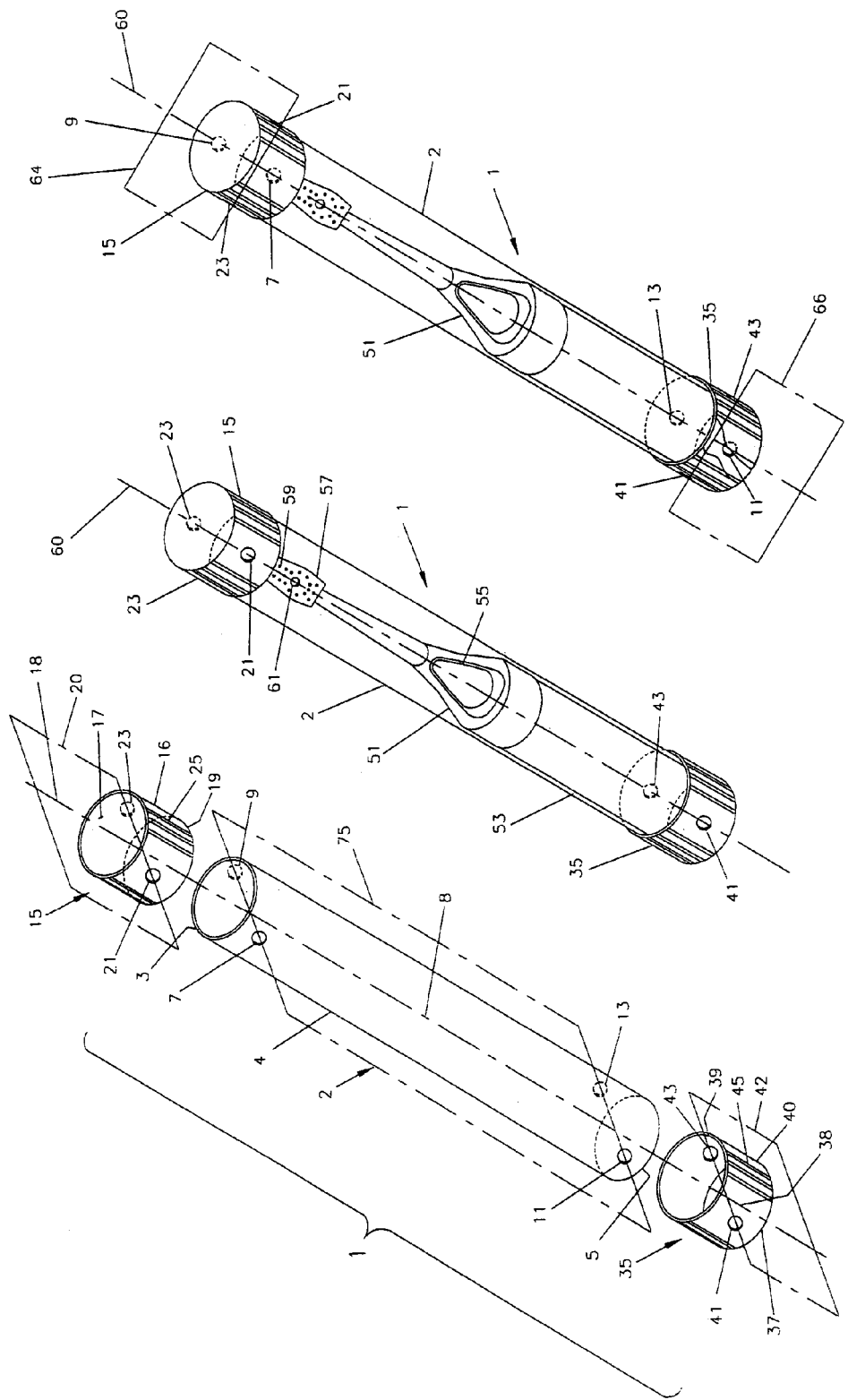
FIG. 6a is an exploded view of a toothbrush container comprising a cylindrical vent-tubing, a top and a bottom vent-cap.
FIG. 6b is a perspective view of the toothbrush container of FIG. 6a enclosing a pump toothbrush with top and bottom vent-caps aligned in open positions.
FIG. 6c is a perspective view of the toothbrush container of FIG. 6a enclosing a pump toothbrush with top and bottom vent-caps aligned in closed positions.

The functions of a toothbrush container of the present invention are illustrated in FIGS. 6a and 6b, which show an exploded view and an assembled view of toothbrush container 1. FIG. 6c shows toothbrush container 1 that encloses pump toothbrush 51. Referring to the exploded view of FIG. 6a, toothbrush container 1 of present invention consists of vent-tubing 2 and top and bottom vent-caps 15 and 35. Vent-tubing 2 having annular cylindrical wall 4 has opposing vent holes 7, 9 at equal distance from top opening end 3 and opposing vent holes 11, 13 at equal distance from bottom opening end 5. Top vent-cap 15 has opposing vent holes 21, 23 at equal distance from closed wall 17 and bottom vent-cap 35 has opposing vent holes 41, 43 at equal distance from closed wall 37. All of the vent holes on the top and the bottom vent-caps are positioned for selectively opening or closing the vent holes of the vent-tube when both vent caps are mounted. With respect to the positions of the opposing holes, the view in FIG. 6a shows that symmetry planes 20 and 42 of the top and the bottom vent-caps 15 and 35 are in plane with the symmetry plane 75 of the vent-tubing 2. All the vent holes are positioned such that when both vent-caps are fully mounted on the vent-tubing with their symmetric planes overlapping with that of the vent-tube, the vent holes of the vent-caps are matched with that of the vent-tube. At this fully vented open position as indicated in FIG. 6c, the bristles are exposed to ambient air for drying. For preventing drying of the toothpaste in the spout opening, vent holes 7, 9 and 11, 13 of the vent-tubing 2 need to be fully closed by top and bottom vent-caps 15 and 35. The most effective closing and sealing of these vent holes are illustrated in FIG. 6b, in which the symmetry planes 64, 66 of the top and the bottom caps 15, 35 are at 90 degree to the symmetry plane 60 of the vent-tubing 2.

For providing snug-fit for sealing the vent holes of a vent-tubing, the top and bottom vent-caps are made of flexible sealing material. In each vent-cap the inside diameter of the annular sidewall should be slightly smaller than the outside diameter of the vent-tubing for achieving slidable frictional fit when the vent-caps are mounted on the vent-tubing. For facilitating twisting of the vent-caps grip ribs 25 and 45 are added to the periphery of the sidewalls of the top and the bottom vent-caps 15 and 35, respectively.

The invention has been described in detail with reference to a preferred embodiment thereof. However, it is understood that variations and modifications can be effected within the spirit and scope of the invention.

I claim:

1. A pump toothbrush for dispensing dentifrice material from a cartridge to a brush head, comprising:

i. a pump head having a pumping chamber comprising a sidewall having an opening there through;

a. an elastic compressible button attached to the sidewall opening, said elastic compressible button returning to its original shape when being released from a depressed position;

b. an outlet connector extending from said sidewall, said outlet connector having a tubular wall and a flow channel;

c. an inlet connector being supported by said sidewall, said inlet connector having an interior surface and an exterior surface, a check valve attached on the interior surface and a recess wall attached to the exterior surface having an inlet opening therethrough, and said inlet opening being in communication with the flow channel of the outlet connector;

ii. a cartridge containing dentifrice material attached to the inlet connector of said pump head, said cartridge having a cylindrical tube and a piston;

iii. a brush head comprising a bristle platform having a spout opening and a plurality of bristles attached and a neck with a base having a flow channel in communication with the spout opening and the flow channel of the outlet connector of said pump head when said base is attached to the tubular wall of said outlet connector;

iv. a slit valve attached to the spout opening, said slit valve opens for dispensing dentifrice material when said elastic compressible button is depressed and said slit valve returns to the closed position when the elastic compressible button is released from a depressed position.

\* \* \* \* \*